United States Patent
Baumgart (10) Patent No.: US 12,042,619 B2
(45) Date of Patent: Jul. 23, 2024

(54) CONNECTOR FOR CONNECTING A FIRST MEDICAL LINE TO A SECOND MEDICAL LINE

(71) Applicant: Fresenius Kabi Deutschland GmbH, Bad Homburg (DE)

(72) Inventor: Steffen Baumgart, Hünfeld (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 815 days.

(21) Appl. No.: 17/056,522

(22) PCT Filed: Jun. 5, 2019

(86) PCT No.: PCT/EP2019/064585
§ 371 (c)(1),
(2) Date: Nov. 18, 2020

(87) PCT Pub. No.: WO2019/243044
PCT Pub. Date: Dec. 26, 2019

(65) Prior Publication Data
US 2021/0213272 A1 Jul. 15, 2021

(30) Foreign Application Priority Data
Jun. 21, 2018 (EP) .................................... 18179095

(51) Int. Cl.
*A61M 39/10* (2006.01)
(52) U.S. Cl.
CPC .................. *A61M 39/1011* (2013.01); *A61M 2039/1033* (2013.01); *A61M 2039/1038* (2013.01); *A61M 2039/1072* (2013.01)
(58) Field of Classification Search
CPC ...... A61M 39/1011; A61M 2039/1033; A61M 2039/1038; A61M 2039/1072;
(Continued)

(56) References Cited

U.S. PATENT DOCUMENTS

| 5,062,648 A | 11/1991 | Gomringer |
| 2003/0151256 A1 | 8/2003 | Guala |

(Continued)

FOREIGN PATENT DOCUMENTS

| CN | 1919368 A | 2/2007 |
| CN | 101189466 A | 5/2008 |

(Continued)

OTHER PUBLICATIONS

International Search Report and Written Opinion, counterpart International Appl. No. PCT/EP2019/064585, dated Jul. 4, 2019 (9 pages).
Chinese First Office Action CN 201980040735.8 dated Jun. 30, 2022 (English translation).

*Primary Examiner* — James D Ponton
(74) *Attorney, Agent, or Firm* — Cook Alex Ltd.

(57) ABSTRACT

A connector for connecting a first medical line to a second medical line is disclosed. This connector comprises an insertion shaft (12) having a flow channel that is intended to be brought into fluid communication with a lumen of a first medical line (3); a collar (10) that circumferentially extends around the insertion shaft (12), wherein the collar (10) comprises a first thread (100) on an inner side that faces the insertion shaft (12); and an elastic member (14) that is placed between the insertion shaft (12) and the collar (10), wherein the elastic member (14) comprises an abutment portion (141) abutting a surface of the insertion shaft (12) and being displaceable relative to the surface of the insertion shaft (12). The collar (10) is radially movable around the insertion shaft (12) and the elastic member (14) comprises a thread portion (142) having a second thread that engages the first thread (100) of the collar (10) such that a rotational movement of the collar (10) around the insertion shaft (12) results in a lateral displacement of the elastic member (14) along the surface of the insertion shaft (12). Furthermore, a (Continued)

method for operating such a connector is disclosed. Additionally, a connector assembly comprising such a connector is disclosed.

14 Claims, 5 Drawing Sheets

(58) Field of Classification Search
CPC .... A61M 2039/1066; A61M 2039/267; A61M 39/1055; A61M 39/165; A61M 39/18; A61M 39/26; A61M 39/10; A61M 2039/1027
See application file for complete search history.

(56) References Cited

U.S. PATENT DOCUMENTS

| | | |
|---|---|---|
| 2006/0192164 A1* | 8/2006 | Korogi .................. A61M 39/26 251/149 |
| 2008/0183155 A1 | 7/2008 | Funamura et al. |
| 2009/0177170 A1 | 7/2009 | Kitani et al. |
| 2010/0100056 A1 | 4/2010 | Cawthon et al. |
| 2016/0001058 A1 | 1/2016 | Ziebol et al. |

FOREIGN PATENT DOCUMENTS

| | | |
|---|---|---|
| CN | 103124582 A | 5/2013 |
| DE | 202006015983 U1 | 3/2007 |
| WO | 2011163124 A1 | 12/2011 |

\* cited by examiner

CONNECTOR FOR CONNECTING A FIRST MEDICAL LINE TO A SECOND MEDICAL LINE

The present invention relates to a connector for connecting a first medical line to a second medical line according to the preamble of claim 1, to a connector assembly comprising a first connector and a second connector according to the preamble of claim 12, and to a method for operating such a connector according to the preamble of claim 14.

A connector of this kind is intended to be connected to a second connector. Thereby, an insertion shaft of the first connector is inserted into an insertion shaft receiving portion of the second connector. If the first connector is in fluid communication with a first medical line and if the second connector is in fluid communication with a second medical line, the first and second medical lines are connected to each other by the first connector and the second connector.

A medical line of this kind may for example be a line used for the enteral feeding of a patient. Enteral feeding generally refers to the delivery of a nutritionally complete feed, containing protein, carbohydrate, fat, water, minerals and vitamins, directly into the stomach, duodenum or jejunum of a patient. A feeding tube, for this purpose, may for example be passed through the nares (nostril), down the esophagus and into the stomach (so-called nasogastric feeding tube). A nasojejunal feeding tube, in comparison, may be passed further through the stomach into the jejunum, the middle section of the small intestine. And a gastric feeding tube is a tube inserted through a small incision in the abdomen into the stomach and is used, preferably, for long-term enteral nutrition.

When using feeding lines for the enteral feeding of a patient, the first line may for example be placed on the patient, for example providing a feeding port to the stomach. This first line may remain on the patient for a rather long time, for example a few days or even a few weeks. The second line may be connected to this first line for the actual feeding, wherein for each feeding procedure a new second line may be used and disposed after the feeding procedure.

A connector assembly in this regard serves to connect the feeding lines to each other. A first connector (also denoted as male connector) herein may be arranged for example on the line placed on the patient, whereas a second connector (female connector) may be used on the second line for connecting the second line to the first line for carrying out an actual feeding procedure.

Whereas the second connector may be used only once for carrying out a feeding procedure, the first connector connected to the line placed on the patient may be re-used multiple times. Because the first connector is re-used multiple times for multiple feeding procedures, it is to be made sure that the first connector is clean when connecting the lines to each other, in order to avoid a contamination of any solution passed towards the patient.

Such cleaning, however, may not be easy, because the insertion shaft of the first (male) connector may actually not be easily accessible. Additionally, when no second connector is connected to the first connector, contaminations can accumulate in a space surrounding the insertion shaft or even within a fluid channel of the insertion shaft.

It is an object of the present invention to provide a connector that is easier to clean and can be more reliably handled than connectors known from prior art.

This object is achieved by a connector for connecting first medical line to a second medical line having the features explained below. Such a connector comprises an insertion shaft that has a flow channel which, in turn, is intended to be brought into fluid communication with the lumen of a first medical line. Thus, the flow channel serves for allowing a fluid to flow through it.

Furthermore, the connector comprises a collar that surrounds the insertion shaft in a circumferential manner. Thereby, the collar comprises a first thread on an inner side. This inner side faces the insertion shaft.

Finally, the connector comprises an elastic member that is placed between the insertion shaft and the collar. Thereby, the elastic member comprises an abutment portion that serves for abutting a surface of the insertion shaft. The abutment portion can be displaced relative to the surface of the insertion shaft.

The connector is characterized in that the collar can be radially moved (rotated) around the insertion shaft and in that the elastic member comprises a threaded portion having a second thread. This second thread engages the first thread of the collar so that a rotational movement of the collar around the insertion shaft is transformed into an axial movement of the elastic member along the surface of the insertion shaft.

The elastic member fills out a whole space that is radially formed between the insertion shaft and the collar surrounding the insertion shaft. In doing so, it effectively prevents contaminations of this space and thus of the thread of the collar. Since the elastic member is only moved if the collar is rotated around the insertion shaft, it cannot be displaced by coincidence. Rather, an active movement of the collar is necessary to displace the elastic member. This enhances the functional reliability of the connector.

Generally, the insertion shaft can have any desired shape. In an embodiment, it has a conical shape. In another embodiment, it has a cylindrical shape. To avoid a rotational movement of the elastic member around the insertion shaft, the insertion shaft and/or the collar, in an embodiment, comprises a protrusion or a recess that prevents the elastic member from rotating around the insertion shaft if the collar is rotated about the insertion shaft. Thus, this protrusion or recess acts as stopper for the elastic member. It might have the the shape of a longitudinally extending tongue.

In an embodiment, the abutment portion has at least partially a ring-shaped cross section and extends around the insertion shaft in a circumferential manner. Thereby, the inner diameter of the abutment portion corresponds, in an embodiment, to the outer diameter of the insertion shaft. Then, the abutment portion tightly abuts against the insertion shaft but can still slide along the surface of the insertion shaft.

In an embodiment, the abutment portion is at least partially received in a guiding recess. The guiding recess may be formed on the insertion shaft or the collar. When the abutment portion is displaced along the insertion shaft, it abuts the guiding recess and is guided by the guiding recess along the insertion shaft.

While it is generally possible that the elastic member only surrounds the insertion shaft and fills out the space formed radially between the insertion shaft and the collar, the elastic member comprises, in an embodiment, a split septum portion covering a terminal portion of the insertion shaft as well as a mouth of a flow channel that is arranged in the terminal portion of the insertion shaft. Then, this split septum securely covers both the terminal portion of the insertion shaft and the mouth of the flow channel and prevents any contaminations from entering the flow channel or gastric fluid leaking the feeding tube. The split septum then serves for a smooth surface and for particularly easy cleaning of the end portion of the connector. Upon rotating the collar, the insertion shaft breaks through the split septum and gets exposed (i.e., the elastic member is retracted towards an inner part of the connector).

To allow an easy relative movement of the insertion shaft and the elastic member, a slit of the split septum can have any appropriate shape. In an embodiment, the slit has the shape of a cross slot or of a star-shaped slot.

In an embodiment, the abutment portion comprises two parts having different diameters. To be more precisely, the first part has a first diameter and the second part has a second diameter, wherein the first diameter is bigger than the second diameter. Thus, the abutment portion has a step-like appearance in this embodiment. Likewise, the insertion shaft has a complementary shape comprising two parts of different diameters.

In an embodiment, the first part is arranged closer to the terminal portion of the insertion shaft than the second part. By such an arrangement, it is possible to prevent the elastic member from unintentionally falling out of the connector. Rather, in such an arrangement, the second part (having a smaller diameter) will abut against portion of the insertion shaft once the elastic member is in its most deployed state.

In an embodiment, the elastic member is made of at least one plastic material. Thus, it comprises or fully consists of this at least one plastic material. Appropriate plastic materials are silicone, silicone rubbers, silicone elastomers, and other elastomers.

In an embodiment, the elastic member is made of at least two different plastic materials. Thereby, the different plastic materials have different elasticities. Thus, the elastic member can be made of a composite material. In such a case, it is possible to adapt the elastic properties of different portions of the elastic member to the individual needs.

In an embodiment, the split septum is made of a first plastic material. In this embodiment, the abutment portion and/or the thread portion is made of the second plastic material. Thereby, the first plastic material is more elastic than the second plastic material. By such choice of plastic materials for producing the different portions of the elastic member, it is possible to produce the split septum such that the insertion shaft can easily break through the split septum if the elastic member moves relative to the insertion shaft. At the same time, it is possible to avoid any undesired deformation of the abutment portion and/or the thread portion so as to allow smooth sliding of the elastic member along the surface of the insertion shaft upon rotation of the collar of the connector.

In an embodiment, the connector can be present in two different states, namely an activated state and a non-activated state. In the activated state, the insertion shaft is exposed. Then, it is possible to connect the connector to another connector. In the non-activated state, the insertion shaft is surrounded or even covered by the elastic member. Then, the elastic member acts like a closure of the space that is formed between the insertion shaft and the surrounding collar and optionally also as a closure of the flow channel being present in the insertion shaft. When the connector is transferred from its non-activated state to its activated state, the elastic member is retracted into an interior of the connector. The insertion shaft is then exposed. When the connector is transferred from its activated state into its non-activated state, the elastic member is deployed from the interior of the connector towards an end portion of the connector. Thereby, excessive substances (such as nutrition and medication) being still present in the space between the insertion shaft and the collar are pushed out of the connector by the deploying elastic member. In the activated state, the elastic member securely surrounds or covers the terminal portion of the insertion shaft. It then provides the connector with a smooth surface that is easy to clean and that is gentle to the skin of the patient.

In an aspect, the present invention relates to a connector assembly comprising a first connector and a second connector. Thereby, the second connector is a connector having an insertion shaft receiving portion and a thread portion. The second connector can also be referred to as female connector. This connector assembly is characterized in that the first connector is a connector according to the preceding explanations. When the first connector and the second connector are connected to each other, the insertion shaft receiving portion of the second connector receives an insertion shaft of the first connector. At the same time, the thread portion of the second connector engages a first thread of a collar of the first connector. Thus, by rotating the collar of the first connector along the thread portion of the second connector (which is typically arranged on an outer surface of the insertion shaft receiving portion), a tight connection between the first connector and the second connector is possible. After such a connection is established, the flow channel of the insertion shaft is in fluid communication with a flow channel within the insertion shaft receiving portion of the second connector. Thereby, the flow channel of the first connector is intended to be in fluid communication with a first medical line, whereas the flow channel of the second connector is intended to be in fluid communication with a second medical line. In such a case, the first medical line and the second medical line are connected to each other in a fluidly tight manner with the aid of the first connector and the second connector, i.e. with the aid of the connector assembly.

In an embodiment, the insertion shaft of the first connector can only be inserted into the insertion shaft receiving portion of the second connector after the first connector has been transferred from its non-activated state into its activated state. Thereby, the terminal portion of the insertion shaft is surrounded or covered by an elastic member in the non-activated state of the first connector, whereas the terminal portion of the insertion shaft is exposed in the activated state of the first connector. A transfer of the first connector from its non-activated state to its activated state (and vice versa) is achieved by rotating the collar around the insertion shaft.

In an aspect, the present invention relates to a method for operating a connector according to the preceding explanations. To be more precisely, this method relates to transferring the connector according to the preceding explanations from a non-activated state into an activated state, or vice versa. This method comprises the steps explained in the following.

A collar, which circumferentially extends around an insertion shaft, is rotated around this insertion shaft either in a first direction or in a second direction. Thereby, the second direction is opposite to the first direction. The insertion shaft comprises a flow channel that is intended to be brought into fluid communication with a lumen of a first medical line. The collar comprises a first thread on an inner side facing the insertion shaft.

By this rotation of the collar, a lateral displacement of an elastic member is achieved. This elastic member is located between the insertion shaft and the collar. The displacement occurs along the surface of the insertion shaft and is effected due to an engagement of a second thread being present on a thread portion of the elastic member with the first thread.

Thus, a rotational movement of the collar is transformed into a lateral (or axial) displacement of the elastic member.

If the collar is rotated in the first direction, the lateral displacement results in a retraction of the elastic member from the terminal portion of the insertion shaft into an interior of the connector. Consequently, the terminal portion of the insertion shaft is exposed. This means that the connector is present in its activated state.

If the collar is rotated in the second direction, the lateral displacement results in a deployment of the elastic member from an interior of the connector towards the terminal portion of the insertion shaft. The elastic member then at least partially covers the terminal portion of the insertion shaft. Then, the connector is in its non-activated state. It is particular appropriate if the elastic member fully covers the terminal portion of the insertion shaft as well as a mouth of a flow channel arranged in the insertion shaft. This can be easily achieved by providing a split septum portion of the elastic member through which the insertion shaft can slide upon a relative movement between the elastic member and the insertion shaft.

It should be noted that a rotation of the collar in the first direction is only possible if the connector is not present in its activated state. Likewise, a rotation of the collar in the second direction is only possible if the connector is not present in its non-activated state. Thus, if the connector is already in its activated state, no further relative movement between the elastic member and the insertion shaft is possible towards the terminal portion of the insertion shaft. Likewise, no further relative movement between the elastic member and the insertion shaft is possible away from the terminal portion of the insertion shaft if the connector is already in its non-activated state.

In an embodiment, at least one of the insertion shaft of the first connector, the elastic member of the first connector, another portion of the first connector and a portion of the second connector comprises antimicrobial characteristics, such as a (solid or liquid) coating of a antimicrobial substance or the like. An antimicrobial substance is a chemical substance which acts against microorganisms and stops their growth. For example, an antibiotic represents an antimicrobial substance to be used against bacteria, and an antifungal represents an antimicrobial substance to be used against fungi. An antimicrobial may be a substance of natural, semi-synthetic or synthetic origin suitable to act against microorganisms.

All embodiments disclosed herein can be combined in any desired way and can be transferred from the disclosed connector to the disclosed connector assembly and to the disclosed method and vice versa in each case.

Figure 1:
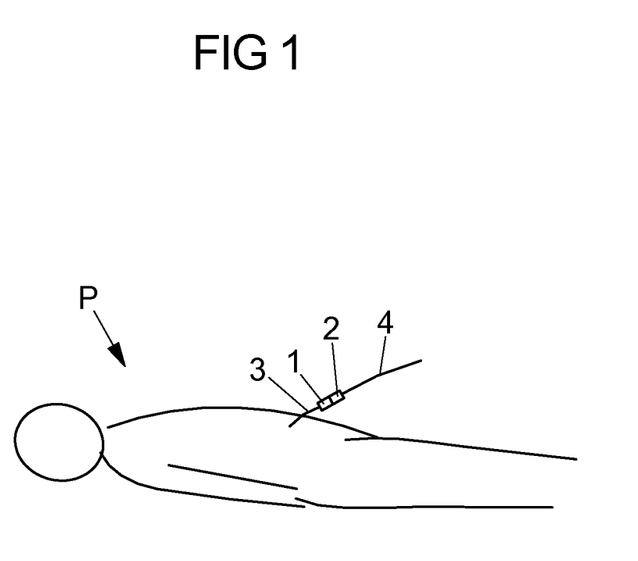
FIG. 1 shows a schematic drawing of a feeding line placed on a patient.

Further details of aspects of the present invention will be explained with respect to embodiments and accompanying figures. In the Figures:

FIG. 1 shows a schematic drawing of a feeding line assembly comprising a first feeding line 3 as first medical line and a second feeding line 4 as second medical line placed on a patient P.

The first and second feeding lines 3, 4 for example serve for providing an enteral feeding to the patient P. For this purpose, the first feeding line 3 may, for example through an incision in the abdomen of the patient P, be inserted into the stomach of the patient P and may be used as a port for a long-term enteral feeding. The second feeding line 4 is connected to the first feeding line 3 via a connector assembly comprising a first connector 1 and a second connector 2. The second feeding line 4 may for example be connected to a container comprising an enteral feeding solution, which is delivered towards the patient P via the first and second feeding lines 3, 4 for example using a suitable pumping device.

Whereas the second feeding line 4 may be used for example only once in connection with the container comprising the enteral feeding solution and may be disposed after use, the first feeding line 3 placed on the patient P may remain on the patient P for a rather long term, for example a few days or even a few weeks, and may be used multiple times to carry out multiple feeding procedures. There hence is a necessity to keep the first feeding line 3 as well as the first connector 1 connected to the first feeding line 3 clean, such that a contamination of the first feeding line 3 and the first connector 1 connected to it is effectively prevented.

Figure 2:
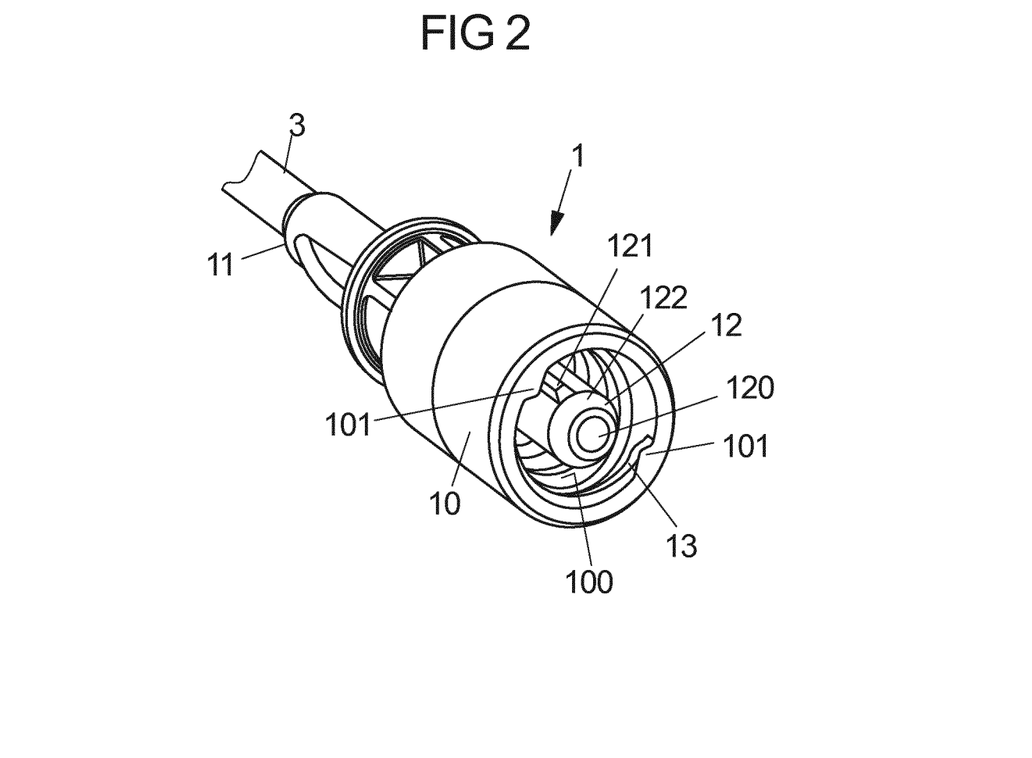
FIG. 2 shows an embodiment of a connector.

An embodiment of the first connector 1 is shown in FIG. 2. The first connector 1, in this embodiment, comprises a cylindrical collar 10 circumferentially extending about a cylindrical insertion shaft 12 in a coaxial manner and forming, together with the insertion shaft 12, a radial inner space 13 between the collar 10 and the insertion shaft 12. On the inner wall of the collar 10 a thread 100 is arranged allowing for a screw type connection with a second connector. The collar 10 can be freely rotated around the insertion shaft 12 but cannot be removed from the insertion shaft 12.

Only for a better illustration of the inner parts of the first connector 1, an elastic body which is located in the radial inner space 13 is not shown in FIG. 2. The insertion shaft 12 comprises a longitudinal tongue 121 extending on the outer surface of the insertion shaft 12 coaxially with a flow channel inside the insertion shaft 12. This tongue 121 serves as protrusion and prevents the elastic member from rotating about the insertion shaft 12.

The insertion shaft 12 can be inserted in an insertion direction into an insertion opening (serving as insertion shaft receiving portion) of a second connector. The insertion shaft 12 has a substantially cylindrical shape having a circular cross section. The insertion opening of a second connector has a corresponding, complementary shape and hence is suited to receive the insertion shaft 12. This is generally known and will not be explained in more detail.

The insertion shaft 12 comprises a flow channel opening 120 serving as flow channel mouth. The corresponding flow channel extends through the insertion shaft 12 and through a channel shaft 11 aligned with the insertion shaft 12, the channel shaft 11 being connected to the associated first feeding line 3.

Figure 3:
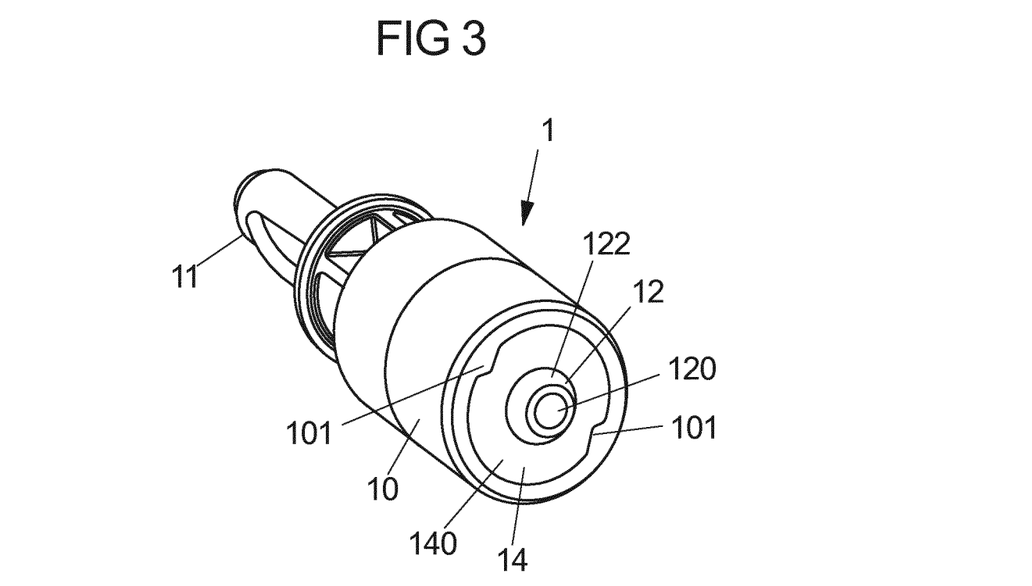
FIG. 3 shows the embodiment of FIG. 2, with an elastic member arranged on the connector.
Figure 4:
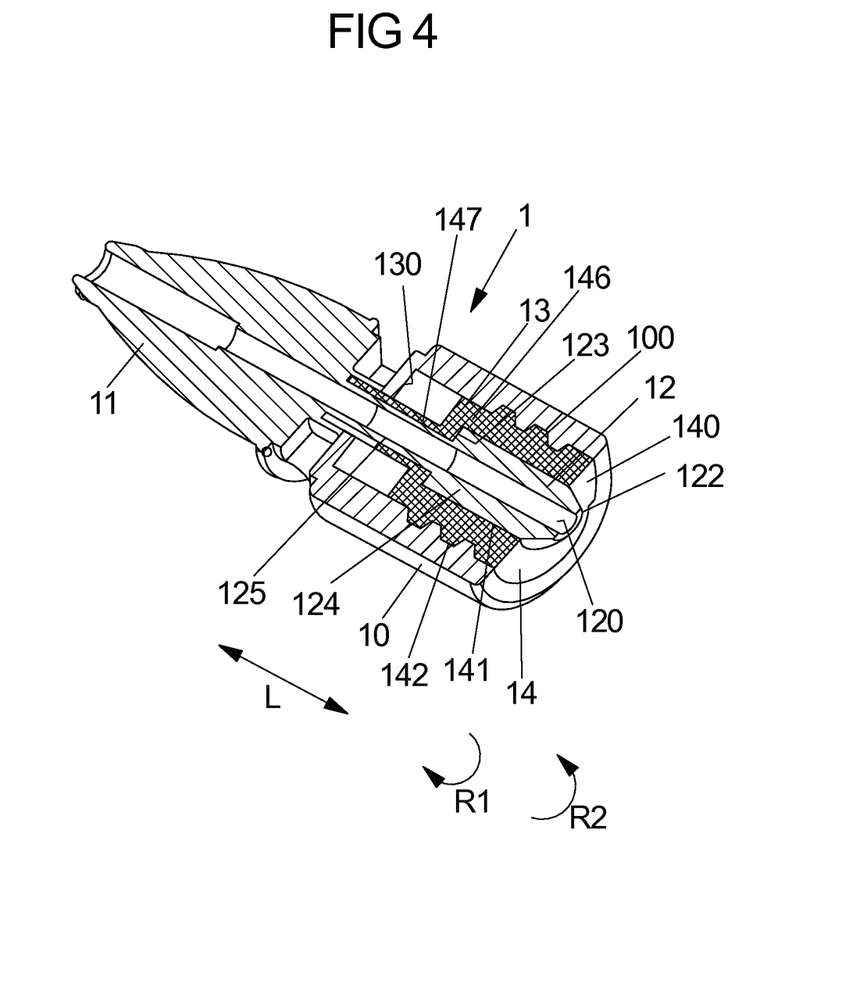
FIG. 4 shows a sectional view of the connector of FIG. 2.

FIG. 3 shows the same first connector 1 like FIG. 2, but additionally illustrates an elastic member 14 which is arranged in the inner radial space 13 between the collar 10 and the insertion shaft 12. FIG. 4 shows a longitudinal cross-section through the first connector 1.

The elastic member 14 comprises an abutment portion 141 having the shape of a hollow cylinder (it is ring-shaped in cross-section) surrounding the insertion shaft 12. A surface 140 of the elastic member is substantially flush with the tip 122 of the insertion shaft 12. This tip 122 is the terminal portion of the insertion shaft 12.

The elastic member 14 comprises a thread portion 142 that has a second thread. This second thread engages the thread 100 of the collar 10 so that the movement of the collar 10 around the insertion shaft 12 serves for a relative movement of the thread 100 and the thread of the thread portion 142. This in turn results in an axial movement of the elastic member 14 along a longitudinal extension direction L of the first connector 1.

Thereby, the elastic member 14 is retracted into an interior of the collar 10 (towards the channel shaft 11), if the collar 10 is rotated in a first direction R1. The maximum movement of the elastic member 14 is limited by a bottom portion 130 of the inner space 13. If the collar 10 is rotated in a second direction R2 opposite to the first direction R1, the elastic member 14 is deployed from the interior of the collar 10 towards the tip 122 of the insertion shaft 12 (away from the channel shaft 11). The maximum movement of the elastic member 14 is limited by a shoulder 123 of the insertion shaft 12. Thus, the insertion shaft 12 does not have an overall uniform outer appearance, but rather comprises a first part 124 having a bigger diameter than a second part 125. The first part 124 is located more distally to the channel shaft 11 than the second part 125 (and thus closer to the tip 122 of the insertion shaft 12). Likewise, the elastic member 14 comprises a first part 146 and a second part 147, wherein a diameter of the first part 146 is bigger than a diameter of the second part 147.

In other embodiments, the shoulder 123 or a comparable element could be rather implemented on the collar instead of on the insertion shaft. Furthermore, the diameters of the individual parts of the insertion shaft depend on the chosen design. If a recess is implemented instead of a protrusion or if the protrusion or recess is provided on the collar instead of on the insertion shaft, different diameter ratios between the individual parts may be chosen.

An axial movement of the elastic member 14 causes the abutment portion 141 to slide along the cylindrical circumferential surface of the insertion shaft 12. If the abutment portion 141 thereby slides towards the tip 122, it swipes away any residuals on the insertion shaft 12 and hence cleans the insertion shaft 12 and the radial inner space 13 from dirt.

Because the surface 140, in the non-activated state of the connector 1 illustrated in FIGS. 3 and 4, is substantially flush with the tip 122 of the insertion shaft 12, dirt and residuals may easily be removed from the elastic member 14 as well as from the insertion shaft 12. In addition, a suitable disinfection for example by using a disinfection solution may be achieved.

In the non-activated state shown in FIGS. 3 and 4 the surface 140 of the elastic member 14 abuts on protrusions 101 protruding radially inwards from the body 10, such that the elastic member assumes a defined axial position with respect to the insertion shaft 12. Since the axial movement of the elastic member 14 is already limited by the shoulder 123 of the insertion shaft 12, such protrusions 101 and not necessary in all embodiments.

The first connector 1 may for example be fabricated from a comparatively hard plastic material, for example by injection molding.

The elastic member 14 may for example be fabricated from an elastic plastic material, for example an elastomer or an elastic foam material. Silicone is particularly appropriate for producing the elastic member 14 or parts thereof.

Figure 5:
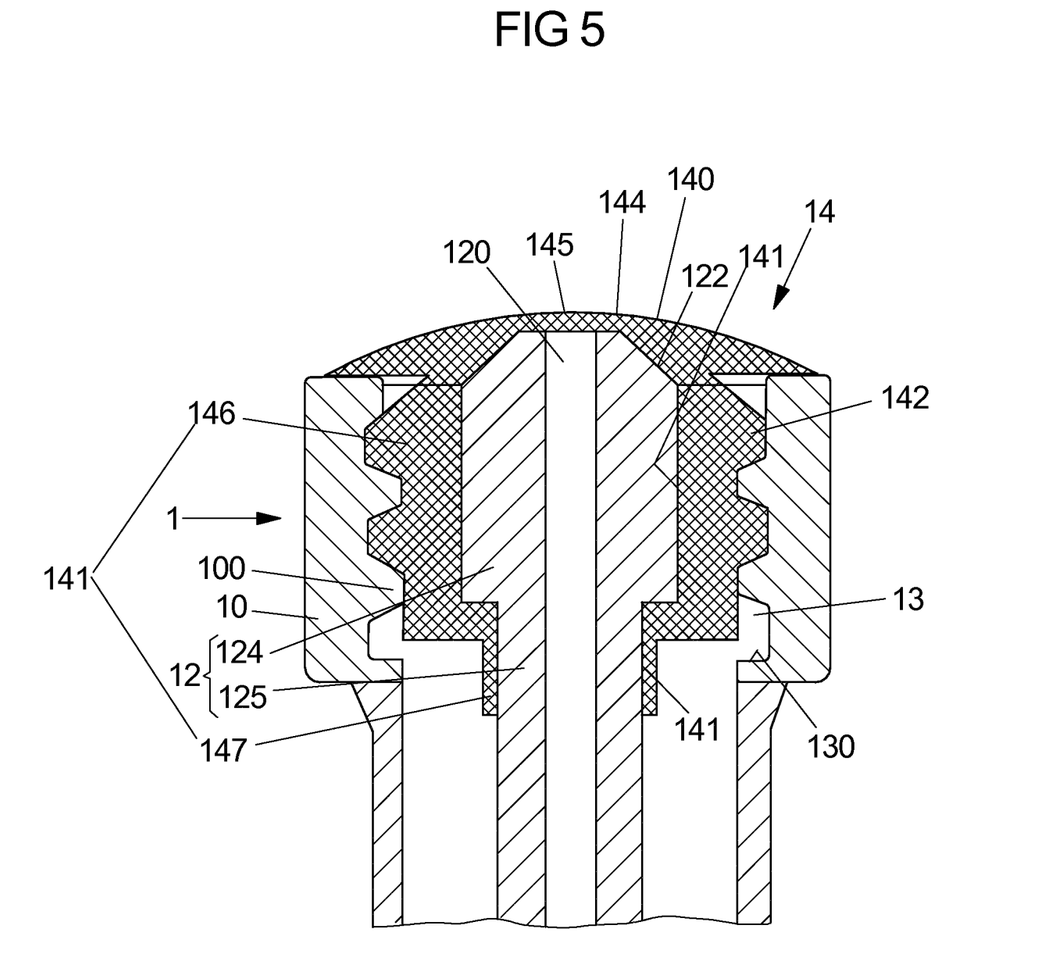
FIG. 5 shows a sectional view of yet another embodiment of a connector in its non-activated state.
Figure 6:
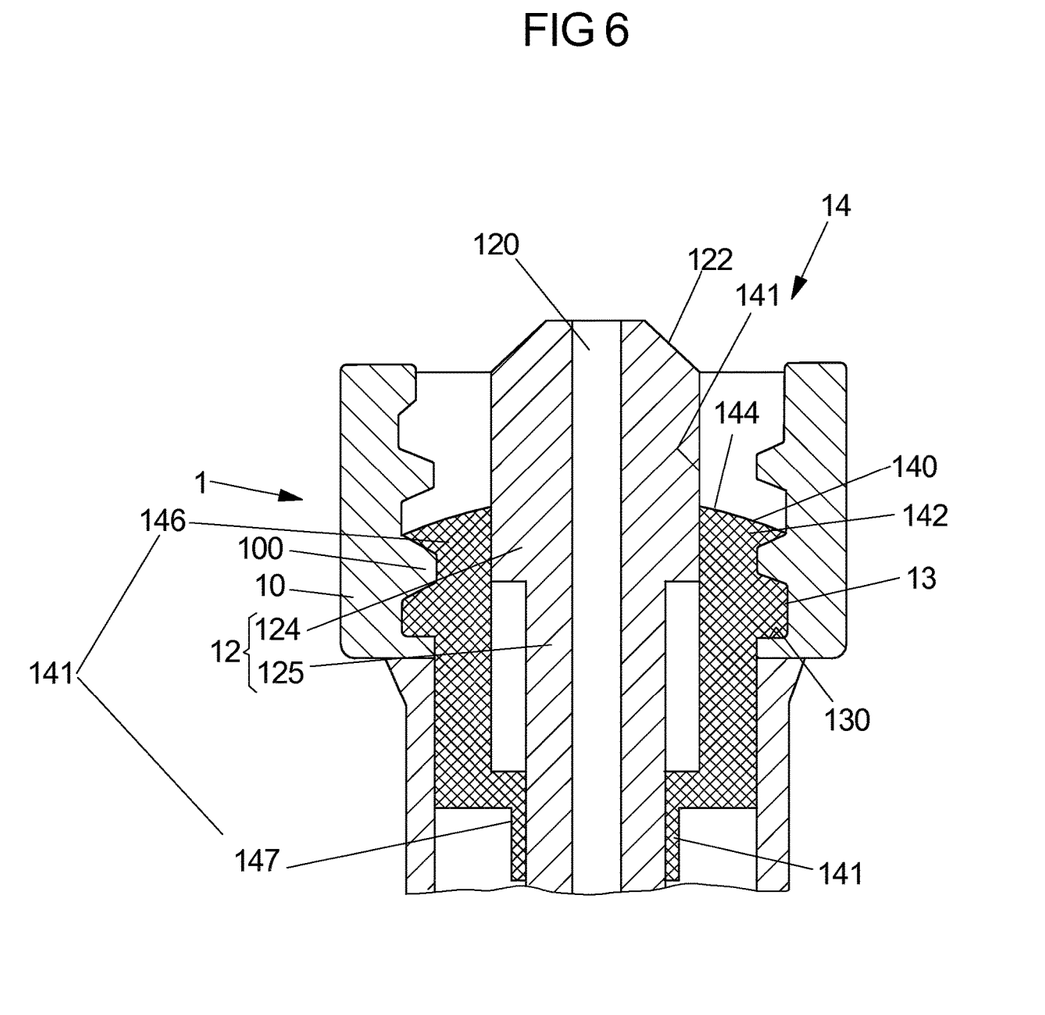
FIG. 6 shows a sectional view of the connector of FIG. 5 in its activated state.

FIGS. 5 and 6 show yet another embodiment of the connector 1 being substantially identical in shape and function as it has been described above. In this respect, reference is made to the explanations given above with respect to FIGS. 2 to 4. FIG. 5 shows the first connector 1 in its non-activated state, and FIG. 6 shows the first connector 1 in its activated state.

In contrast to the afore-described embodiments, in the embodiment of FIGS. 5 and 6 the first connector 1 has an elastic member 14 having a cover-like appearance. To be more precisely, the elastic member 14 comprises a split septum 144 covering the tip 122 of the insertion shaft 12 and the flow channel opening 120 of the first connector 1. The elastic member 14 hence, in a collar-like fashion, provides for a covering of the insertion shaft 12 and the channel opening 120 formed in the insertion shaft 12, such that the insertion shaft 12 with its channel opening 120 is sealed towards the outside. Herein, the surface 140 of the split septum 144 facing towards the outside is easily cleanable by swabbing using a suitable swabbing cloth. In addition, an easy disinfection by applying a suitable disinfection solution is possible.

The split septum 144 comprises a slit 145 at which the septum 144 may be split. The split septum 144 hence, upon rotating the collar 10 about the insertion shaft 12, may be deformed such that the insertion shaft breaks through the split septum 144. The spilt septum 144 is then moved along the insertion shaft 12 into the radial inner space 13 formed in between the insertion shaft 12 and the collar 10 of the first connector 1, as this is shown in FIG. 6 illustrating the first connector 1 in its activated state. The split septum 144 hence is pressed into the inner space 13, the edges of the slit 145 closely and resiliently abutting the circumferential outer surface of the insertion shaft 12, thus providing for a swiping away of any residuals on the insertion shaft 12 and hence a cleaning of the insertion shaft 12 from contaminations.

When the collar 10 is rotated in the opposite direction, the split septum 144 is reset to its original, non-deformed state of FIG. 5 by moving the elastic member 14 back towards the tip 122 of the insertion shaft 12. This movement of the elastic member 14 causes also the split septum 144 to be moved along the circumferential outer surface of the insertion shaft 12 towards the original state of FIG. 5. By this movement again a cleaning of the surface of the insertion shaft 12 is provided, and residuals are removed from the insertion shaft 12.

Once the split septum 144 has reached its original state according to FIG. 5, the insertion shaft 12 and the channel opening 120 formed therein are resealed, hence effectively preventing a contamination.

The invention is not limited to the embodiments described above, but may be implemented in an entirely different fashion.

For example, a connector of the kind described herein may not only be used for enteral feeding, but may be used for connecting any medical lines to each other for transferring medical solutions, such as medication, nutritional solutions, saline solutions or any other solutions.

The invention claimed is:

1. A connector for connecting a first medical line to a second medical line, the connector comprising:
    an insertion shaft having a flow channel that is intended to be brought into fluid communication with a lumen of a first medical line,
    a collar that circumferentially extends around the insertion shaft, wherein the collar comprises a first thread on an inner side that faces the insertion shaft, and an elastic member that is placed between the insertion shaft and the collar, wherein the elastic member comprises an abutment portion abutting a surface of the insertion shaft and being displaceable relative to the surface of the insertion shaft, characterized in that the collar is rotatably movable around the insertion shaft and in that the elastic member comprises a thread portion having a second thread that engages the first thread of the collar such that a rotational movement of the collar around the insertion shaft results in a lateral displacement of the elastic member along the surface of the insertion shaft.

2. The connector according to claim 1, characterized in that the insertion shaft and/or the collar comprises a recess or a protrusion that prevents the elastic member from rotating around the insertion shaft if the collar is rotated around the insertion shaft.

3. The connector according to claim 1, characterized in that the abutment portion at least partially has a ring-shaped cross section and extends circumferentially around the insertion shaft.

4. The connector according to claim 1, characterized in that the abutment portion is at least partially received in a guiding recess of the insertion shaft or the collar along which the abutment portion is displaceable.

5. The connector according to claim 1, characterized in that the elastic member comprises a split septum portion covering a terminal portion of the insertion shaft and a mouth of the flow channel is arranged in the terminal portion of the insertion shaft.

6. The connector according to claim 5, characterized in that the split septum portion is made of a first plastic material and in that the abutment portion and/or the thread portion are made of a second plastic material, wherein the first plastic material has a higher elasticity than the second plastic material.

7. The connector according to claim 1, characterized in that the abutment portion comprises a first part having a first diameter and a second part having a second diameter, wherein the first diameter is bigger than the second diameter.

8. The connector according to claim 7, characterized in that the first part is arranged closer to a terminal portion of the insertion shaft than the second part.

9. The connector according to claim 1, characterized in that the elastic member is made of at least one plastic material.

10. The connector according to claim 1, characterized in that the elastic member is made of at least two different plastic materials having different elasticities.

11. The connector according to claim 1, characterized in that it can be present in a non-activated state and in an activated state, wherein a terminal portion of the insertion shaft is surrounded and/or covered by the elastic member in the non-activated state but is exposed in the activated state.

12. A connector assembly comprising a first connector and a second connector, wherein the second connector is a connector having an insertion shaft receiving portion and a thread portion, characterized in that the first connector is a connector according to any of the preceding claims, wherein the insertion shaft receiving portion of the second connector receives the insertion shaft of the first connector and the thread portion of the second connector engages the first thread of the collar of the first connector, when the first connector and the second connector are connected to each other.

13. The connector assembly according to according to claim 12, characterized in that a connection between the first connector and the second connector is only possible after the first connector has been transferred from a non-activated state into an activated state, wherein a terminal portion of the insertion shaft is surrounded by the elastic member of the first connector in the non-activated state but is exposed and can be received by the insertion shaft receiving portion in the activated state.

14. A method for transferring a connector according claim 1 from a non-activated state into an activated state, or vice versa, comprising the following steps:
  rotating the collar, which circumferentially extends around the insertion shaft, in a first direction (R1) or in a second direction (R2) opposite to the first direction (R1) around the insertion shaft thereby laterally displacing the elastic member that is placed between the insertion shaft and the collar along the surface of the insertion shaft due to an engagement of the second thread of the thread portion of the elastic member with the first thread, wherein, if the collar is rotated in the first direction (R1), the lateral displacement results in a retraction of the elastic member from a terminal portion of the insertion shaft and in an exposure of the terminal portion of the insertion shaft, so as to obtain the connector in its activated state,
  wherein, if the collar is rotated in the second direction (R2), the lateral displacement results in a deployment of the elastic member towards the terminal portion of the insertion shaft and in an at least partial covering of the terminal portion of the insertion shaft, so as to obtain the connector in its non-activated state,
  wherein a rotation of the collar in the first direction (R1) is only possible if the connector is not present in its activated state and a rotation of the collar in the second direction (R2) is only possible if the connector is not present in its non-activated state.

* * * * *